United States Patent
Halanski et al.

(10) Patent No.: US 10,993,859 B2
(45) Date of Patent: May 4, 2021

(54) CAST SAW PROTECTIVE SYSTEM

(71) Applicants: Matthew Aaron Halanski, Cross Plains, WI (US); Kenneth John Noonan, Madison, WI (US)

(72) Inventors: Matthew Aaron Halanski, Cross Plains, WI (US); Kenneth John Noonan, Madison, WI (US); Jamie Spellman, Massapequa, NY (US); William Richard Greisch, III, Appleton, WI (US); Timothy Allen Abbott, Grayslake, IL (US); Jacob Thomas Bartosiak, Brookfield, WI (US); Amanda Rose Cave, Commack, NY (US); John William Kemnitz, Brookfield, WI (US); Therese Besser, Woodbury, MN (US); Hannah Ruth Frank, Wauwatosa, WI (US); Jeffrey Jiajun Wu, Skokie, IL (US)

(73) Assignees: Matthew Aaron Halanski, Cross Plains, WI (US); Kenneth John Noonan, Madison, WI (US)

(*) Notice: Subject to any disclaimer, the term of this patent is extended or adjusted under 35 U.S.C. 154(b) by 80 days.

(21) Appl. No.: 16/166,565

(22) Filed: Oct. 22, 2018

(65) Prior Publication Data
US 2019/0183696 A1 Jun. 20, 2019

Related U.S. Application Data

(60) Provisional application No. 62/598,555, filed on Dec. 14, 2017.

(51) Int. Cl.
*A61F 15/02* (2006.01)
*B27B 9/02* (2006.01)
(Continued)

(52) U.S. Cl.
CPC ............ *A61F 15/02* (2013.01); *B23D 59/005* (2013.01); *B27B 9/02* (2013.01); *F16P 3/12* (2013.01); *G08B 3/00* (2013.01); *G08B 5/36* (2013.01)

(58) Field of Classification Search
CPC ..... A61F 15/02; B23D 59/005; B23D 59/006; B27B 9/02; F16P 3/12; G08B 3/00;
(Continued)

(56) References Cited

U.S. PATENT DOCUMENTS 4,162,526 A * 7/1979 Gass .................. G05F 1/577
714/22
4,322,724 A * 3/1982 Grudzinski ........... H02M 3/338
331/112

(Continued)

FOREIGN PATENT DOCUMENTS

EP 0541859 5/1993
GB 2068829 A * 8/1981 ......... B23Q 11/0825

OTHER PUBLICATIONS

Cast Saw Skin Injury Eliminator, Final Report, Department of Biomedical Engineering, University of Wisconsin-Madison, Frank et al., May 7, 2014, 29 pages.
(Continued)

*Primary Examiner* — Ghassem Alie
(74) *Attorney, Agent, or Firm* — Bell & Manning, LLC

(57) ABSTRACT

A protective system for a cast saw includes a voltage source and a processor coupled to the voltage source. The processor is configured to apply a voltage to a saw blade of a cast saw. The processor is also configured to receive a voltage reading taken across a conductive layer that is at least partially embedded in a cast. The processor is also configured to determine whether the received voltage reading exceeds a threshold voltage. Responsive to a determination that the received voltage exceeds the threshold voltage, the proces- (Continued)

sor is further configured to activate an alarm to warn a user of the cast saw that the saw blade is in contact with the conductive layer.

19 Claims, 5 Drawing Sheets

(51) Int. Cl.
*B23D 59/00* (2006.01)
*F16P 3/12* (2006.01)
*G08B 5/36* (2006.01)
*G08B 3/00* (2006.01)

(58) Field of Classification Search
CPC .... G08B 5/36; B23Q 11/0046; B23Q 17/225; B23Q 11/0825; B23Q 16/005; A61B 2017/00902
USPC ......... 83/60, 62.1, 63, 66; 30/390, 392–394, 30/208–209; 192/116.5, 129 A, 129 R
See application file for complete search history.

(56) References Cited

U.S. PATENT DOCUMENTS

| | | | | |
|---|---|---|---|---|
| 4,421,111 A * | 12/1983 | Rothman | ................ | A61F 15/02 30/124 |
| 4,543,718 A * | 10/1985 | Duescher | ................ | A61F 15/02 30/124 |
| 4,637,391 A * | 1/1987 | Schlein | ................... | A61F 15/02 30/133 |
| 4,694,686 A * | 9/1987 | Fildes | ................ | G05B 19/4065 324/71.1 |
| 4,744,241 A * | 5/1988 | Mayer | ................... | B23Q 17/09 73/104 |
| 4,976,034 A * | 12/1990 | Whitman | ............. | B23D 45/003 30/124 |
| 5,020,226 A * | 6/1991 | Chabbert | ................ | A61F 15/02 30/390 |
| 5,115,567 A * | 5/1992 | Yang | ...................... | A61F 15/02 30/166.3 |
| 5,435,066 A * | 7/1995 | Bare | ........................ | A61F 15/02 30/388 |
| 5,669,809 A * | 9/1997 | Townsend | .............. | A22C 17/12 307/326 |
| 5,809,362 A * | 9/1998 | Tsuji | ..................... | G03D 3/132 396/571 |
| 6,481,939 B1 * | 11/2002 | Gillespie | ............ | B23Q 17/2233 408/1 R |
| 6,558,394 B2 * | 5/2003 | Lee | ......................... | A61F 13/04 30/390 |
| 6,922,153 B2 * | 7/2005 | Pierga | .................. | B23D 45/067 340/686.5 |
| 7,077,039 B2 * | 7/2006 | Gass | ..................... | B23D 59/005 192/125 R |
| 7,171,879 B2 * | 2/2007 | Gass | ........................ | B23Q 5/58 83/477.1 |
| 7,270,890 B2 * | 9/2007 | Sabol | ........................ | C23C 4/18 428/632 |
| 7,290,472 B2 * | 11/2007 | Gass | ........................ | B27B 5/38 83/397.1 |
| 7,347,131 B2 * | 3/2008 | Gass | ..................... | B23D 47/08 83/58 |
| 7,373,863 B2 * | 5/2008 | O'Banion | .............. | B23D 47/08 192/129 R |
| 7,481,140 B2 * | 1/2009 | Gass | ..................... | B23D 59/001 318/469 |
| 7,661,343 B2 * | 2/2010 | Gass | ..................... | B23D 59/001 188/73.1 |
| 7,681,479 B2 * | 3/2010 | Gass | ..................... | B23D 47/08 83/471.3 |
| 7,698,976 B2 * | 4/2010 | Gass | ..................... | B23D 47/08 83/397.1 |
| 7,739,934 B2 * | 6/2010 | Tetelbaum | ........... | B23D 59/001 700/1 |
| 7,848,799 B2 * | 12/2010 | Herndon | ............ | A61B 17/1695 600/547 |
| 8,051,758 B2 * | 11/2011 | Eppard | ................... | F16D 65/18 192/129 A |
| 8,069,757 B2 * | 12/2011 | Ross | ....................... | A61F 15/02 30/370 |
| 8,490,527 B2 * | 7/2013 | Gass | .................... | B23D 59/001 83/367 |
| 9,022,964 B2 * | 5/2015 | Perrier | .................... | A61F 15/02 602/5 |
| 9,095,469 B2 * | 8/2015 | Nayak | .................... | B23D 47/02 |
| 9,112,408 B2 * | 8/2015 | Blau | ....................... | H02M 1/32 |
| 9,168,188 B2 * | 10/2015 | Zwirkoski | ............... | A61F 15/02 |
| 9,345,487 B2 * | 5/2016 | Herndon | ............... | A61B 5/053 |
| 10,039,663 B2 * | 8/2018 | Liden | ................... | A61F 5/0195 |
| 10,617,416 B2 * | 4/2020 | Leimbach | ........ | A61B 17/07207 |
| 10,624,633 B2 * | 4/2020 | Shelton, IV | ....... | A61B 17/0686 |
| 10,639,036 B2 * | 5/2020 | Yates | ..................... | A61B 34/76 |
| 2007/0243380 A1 * | 10/2007 | Vegad | ..................... | D01F 1/103 428/379 |
| 2010/0294098 A1 * | 11/2010 | Nakadate | ............... | A01D 75/20 83/62.1 |
| 2011/0011517 A1 * | 1/2011 | Wood | .................... | A61F 13/041 156/85 |

OTHER PUBLICATIONS

Kemnitz et al. Improved Cast Liner, Final Report, Department of Biomedical Engineering, University of Wisconsin-Madison, BME Design 200/300, Dec. 14, 2016, 31 pages.
Halanski et al., "How to Avoid Cast Saw Complications," Pediatr Orthop, vol. 36, No. 4, Supplement 1, Jun. 2016, pp. S1-S5.
Monroe et al. "Cast-Saw Injuries: Assessing Blade-to-Skin Contact During Cast Removal: Does Experience or Education Matter?", The Physician and Sportsmedicine, vol. 42, Issue 1, Feb. 2014, pp. 36-44.
Shore et al., "Epidemiology and Prevention of Cast Saw Injuries," The Orthopaedic for, The Journal of Bone and Join Surgery, Inc., 2014, pp. e31(1)-e31(8).
Stork et al., "To Cast, to Saw, and Not to Injure: Can Safety Strips Decrease Cast Saw Injuries?" Clin Orthop Relat Res, vol. 474, No. 2, Feb. 4, 2016, 12 pages.
M. Halanski and K. Noonan, "Cast and splint immobilization: Complications," The Journal of the American Academy of Orthopaedic Surgeons, Jan. 2008, pp. 30-40.

\* cited by examiner

CAST SAW PROTECTIVE SYSTEM

CROSS-REFERENCE TO RELATED APPLICATION

The present application claims the priority benefit of U.S. Provisional Patent App. No. 62/598,555 filed on Dec. 14, 2017, the entire disclosure of which is incorporated by reference herein.

BACKGROUND

A cast is used in the medical field to immobilize a broken or otherwise injured bone. The immobilization allows the injured bone to be set in a proper position and eventually heal, often over the course of weeks or months. The cast is typically formed from multiple layers of material, with an outermost layer of the cast usually being a hard material such as plaster or fiberglass. To remove the cast, physicians typically use a cast saw, which is an oscillating saw specifically designed to cut through casts.

SUMMARY

An illustrative protective system for a cast saw includes a voltage source and a processor coupled to the voltage source. The processor is configured to apply a voltage to a saw blade of a cast saw. The processor is also configured to receive a voltage reading taken across a conductive layer that is at least partially embedded in a cast. The processor is also configured to determine whether the received voltage reading exceeds a threshold voltage. Responsive to a determination that the received voltage exceeds the threshold voltage, the processor is further configured to activate an alarm to warn a user of the cast saw that the saw blade is in contact with the conductive layer.

An illustrative method includes applying, by a processor coupled to a voltage source, a voltage to a saw blade of a cast saw. The method also includes receiving a voltage reading taken across a conductive layer of a cast that is to be sawed open by the cast saw. The method also includes determining, by the processor, whether the received voltage reading exceeds a threshold voltage. Responsive to a determination that the received voltage exceeds the threshold voltage, the method further includes activating an alarm to warn a user of the cast saw that the saw blade is in contact with the conductive layer.

Other principal features and advantages of the invention will become apparent to those skilled in the art upon review of the following drawings, the detailed description, and the appended claims.

BRIEF DESCRIPTION OF THE DRAWINGS

Illustrative embodiments will hereafter be described with reference to the accompanying drawings, wherein like numerals denote like elements. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

A cast is typically formed from multiple layers of material. As an example, a typical cast can include a netting layer adjacent to the patient skin, which can be in the form of a sock, stockinette, or other thin cloth. The netting layer is used to provide comfort and to help with breathability of the overall construct. The cast can also include a padding layer adjacent to the netting layer, and the padding layer can be composed of cotton or another material. A hard outer layer of the cast is often formed from plaster or fiberglass and is used to ensure immobilization of the injured bone or bones.

A cast saw, which as discussed above is typically an oscillating saw, is used to remove a cast once the injury covered by the cast has healed. An oscillating saw operates by rapidly vibrating the saw blade such that the teeth of the saw blade cut through material, as opposed to a rotary saw which operates by rapidly rotating the saw blade. The cast removal process involves making one or more cuts through the cast with the cast saw so that it can be removed. The cuts made with the cast saw generally run along the length of the cast longitudinally as opposed to across the width of the cast. Although cast saws are designed to be safe for the patient, it is well documented that injuries can and do occur during the cast removal process. One injury is in the form of a cut/abrasion from direct contact with the oscillating saw blade to the patient's skin. This type of injury can occur if the physician (or other operator of the cast saw) saws all the way through the cast without realizing it and continues to apply pressure such that the saw blade directly contacts the patient's skin. Another injury that can occur is a thermal injury or burn. Thermal injury occurs when friction between the oscillating saw blade and the cast material causes the blade and cast material to heat up excessively in proximity to the patient's skin. Thermal injury can also result from direct contact of the saw blade to the patient's skin.

Described herein are systems and methods for preventing injury to patients during the cast removal process. In an illustrative embodiment, the proposed systems and methods involve use of a conductive layer within the cast to form a circuit with the cast saw when the saw blade contacts the conductive layer. The formed circuit is used to alert the operator that he/she has sawed through the cast and contacted the conductive layer. Specifically, in one embodiment, a voltage is applied to the saw blade and the voltage across the conductive layer is monitored. If the saw blade contacts the conductive layer, the voltage applied to the saw blade causes an increase in the voltage measured across the conductive layer. This increase in measured voltage triggers an alarm that informs the user to stop the cast saw.

Figure 1:
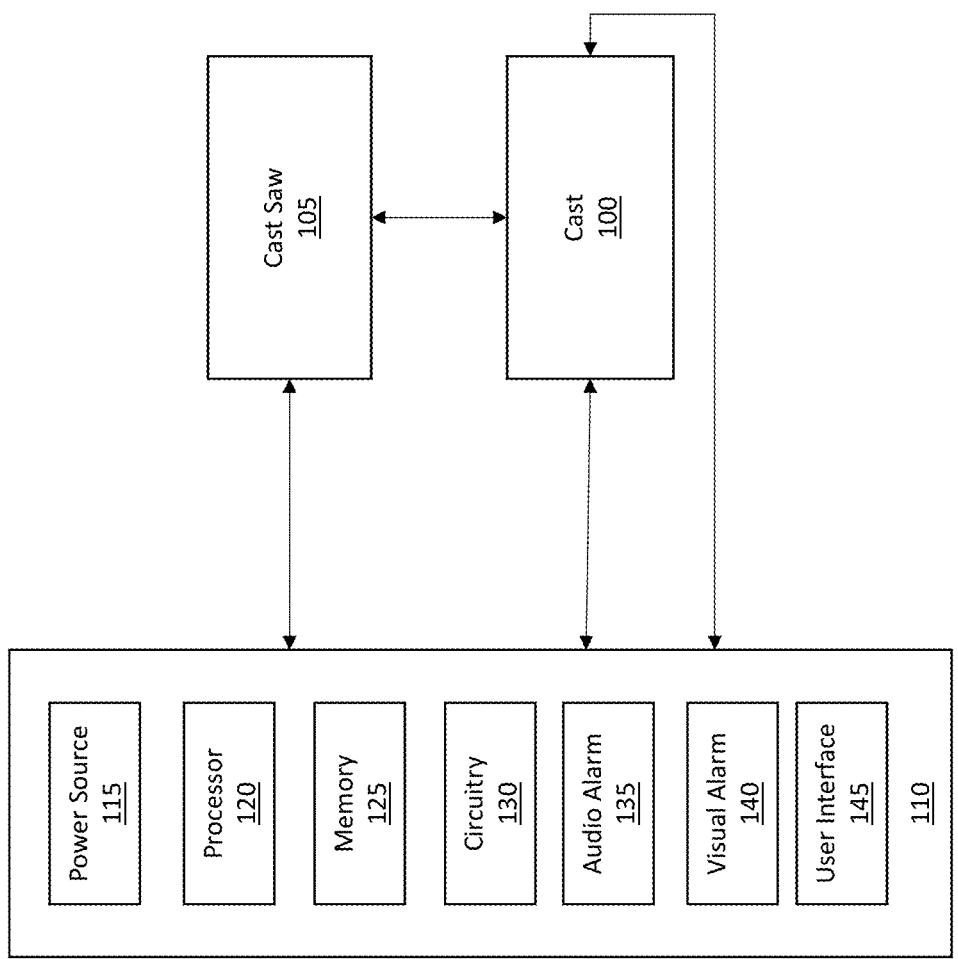
FIG. 1 is a block diagram depicting a system for performing cast removal in accordance with an illustrative embodiment.

FIG. 1 is a block diagram depicting a system for performing cast removal in accordance with an illustrative embodiment. The system includes a cast 100, a cast saw 105, and a control system 110. In alternative embodiments, the system can include additional, fewer, and/or different components. The cast 100 includes a conductive layer that in one embodiment is positioned adjacent to the patient's skin. In an alternative embodiment, the conductive layer may be embedded between layers of the cast 100. In at least some embodiments, the cast also includes a padding layer proximate the conductive layer, and a hard external layer covering the padding layer. The padding layer and hard external layer can be made from standard materials and these layers can be formed and applied using standard procedures. In an illustrative embodiment, the conductive layer can be formed from one or more breathable materials to help improve the patient's comfort.

Figure 2:
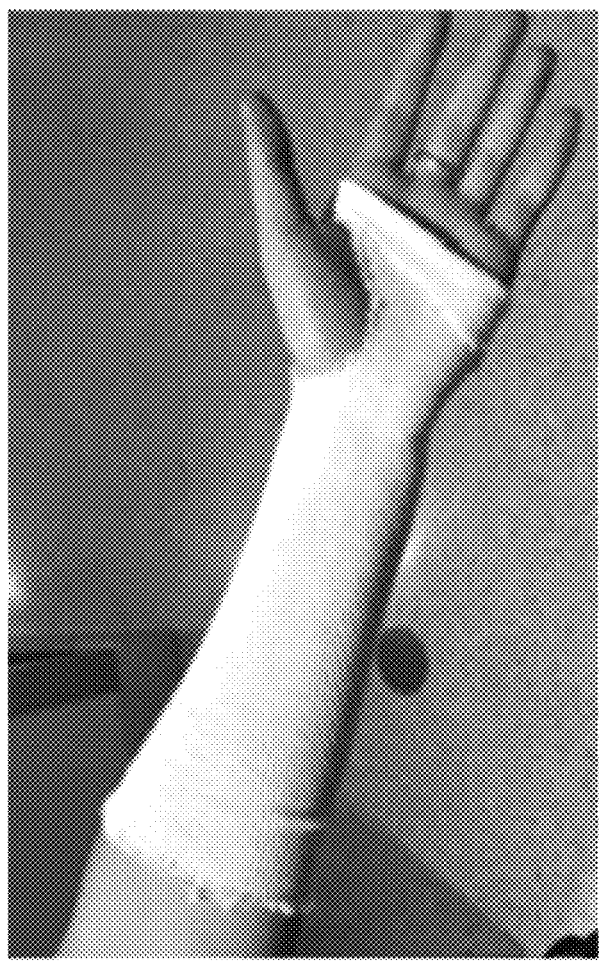
FIG. 2 depicts a conductive layer for a cast in the form of a stockinette in accordance with an illustrative embodiment.

In another illustrative embodiment, the conductive layer is in the form of a stockinette, such as the stockinette depicted in FIG. 2. As shown, the stockinette covers the entire area of skin which is under the cast, which improves the overall safety of the system because the user does not need to keep the saw centered over a specific area of the cast. As depicted in FIG. 2, the stockinette includes a thumb hole and covers a portion of the patient's hand. Alternatively, the thumb hole may not be included and the stockinette may cover just a portion of an arm, leg, body, neck, etc. In other alternative embodiments, the conductive layer can be in the form of a wrap (i.e., a long strip of material that is wrapped around the injured bone), one or more conductive strips of material (e.g., silicon) incorporated into the cast, a conductive tape applied within the cast, etc.

In one embodiment, the conductive layer can be formed by a composite fabric made of 76% nylon and 24% elastic fiber, and coated with medical grade silver such that the surface resistivity is approximately 0.5 ohm/square inch. As a result of this composition, the conductive layer is able to stretch in multiple directions, and is able to conform to many different cast sizes. In one embodiment, only one side of the conductive layer is coated with silver (or another metal). Through testing, it has been determined that coating just one side results in approximately the same surface resistivity on both sides (i.e., the inside and outside) of the stockinette. Alternatively, both sides may be coated with metal. In other embodiments, different ratios of nylon to elastic fiber may be used, such as 75% to 25%, 70% to 30%, 80% to 20%, etc. In other alternative embodiments, a different type or types of material may be used such as a semitransparent polyester fabric coated with pure silver and having interwoven copper threads, a cotton fabric coated with silver, silicon strips, silicon infused with graphite, etc. Different biocompatible metals may also be used to impart the desired conductivity onto the conductive layer such as gold, copper, nickel, etc. Additionally, different resistivities can also be imparted onto the conductive layer.

In an illustrative embodiment, the conductive layer can have a small measurable voltage across its surface. The amount of voltage across the surface of the conductive layer can depend on a number of factors, including the material(s) used to coat the cloth portion of the conductive layer, the type of cloth used to form the cloth portion, the amount that the cloth is stretched, the direction in which the cloth is stretched, etc. In one embodiment, these factors can be controlled such that the measurable voltage across the conductive layer is less than 200 milliVolt (mV). Alternatively, a different voltage value may be used.

Depending on the type and location of the injury and the size of the patient, different sizes of casts will be used on different patients, which results in different sizes of the stockinette. Because the system relies on a measured voltage across the stockinette, it is important that the inherent voltage across the stockinette does not vary significantly based on the size thereof. While the inventors have determined that the resistance across the stockinette increases linearly as the area of the stockinette increases, it has also been determined that the resistance will remain sufficiently low for standard cast sizes. The inventors have also determined that the resistance of the stockinette decreases as the stockinette is stretched. Specifically, the resistance follows a trend of exponential decay and approaches a minimum value of ~60% of its original value as the stockinette is stretched to its maximum, which is about 140% of its original length. This decrease in resistance due to stretching does not result in significant variance in the inherent voltage of the stockinette, and therefore does not affect operation of the system.

In an illustrative embodiment, the conductive layer of the cast 100 is connected to the control system 110 via first and second conductive leads (or wires). The first conductive lead can be attached to a first end of the conductive layer and the second conductive lead can be attached to a second end of the conductive layer. These conductive leads allow the voltage across the conductive layer to be measured and monitored by the control system 110. The conductive leads can be attached to the respective ends of the conductive layer via conductive clips, conductive adhesive pads, conductive pins, male/female connections, etc. To make attachment easier, the cast 100 can be constructed such that the ends of the conductive layer extend past the edges of the hard exterior layer, and are easily accessible to the leads.

The cast saw 105 can be a standard oscillating cast saw and can include a standard metallic saw blade. In an illustrative embodiment, a third conductive lead (or wire) connects the control system 110 and the cast saw 105. The third conductive lead is mounted to the cast saw 105 such that the lead is in direct or indirect (conductive) contact with the saw blade. The control system 110 is used to deliver a voltage to the third conductive lead, which in turn is delivered to the saw blade. As a result of this applied voltage to the third conductive lead, any contact of the conductive layer of the cast 100 by the saw blade will increase the voltage across the conductive layer. This increase in voltage across the conductive layer can be detected by the control system 110 due to an increase of the measured voltage between the first and second leads. The detected increase can then be used to trigger one or more alarms, as discussed in more detail below. As discussed in more detail below, the components of the protective system can be incorporated into the cast saw in an alternative embodiment.

The control system 110 includes a power source 115, a processor 120, a memory 125, circuitry 130, an audio alarm 135, a visual alarm 140, and a user interface 145. The power source 115 can be a battery or other electrical component capable of storing or generating a voltage. In one embodiment, the power source 115 can be an electrical plug and cord that receives power from an electrical outlet. The power source 115 can be used to provide power to the various components of the control system 110, including the circuitry 130, the processor 120, audio alarm 135, the visual alarm 140, and the user interface 145.

The processor 120 can be any type of computer processor known in the art. Likewise, the memory 125 can be any type of computer-readable storage medium known in the art. The memory 125 can be used to store operating code and other information in the form of computer-readable instructions. The processor 120 is configured to access the computer-readable instructions stored in the memory 125 and to execute the computer-readable instructions to perform the various operations described herein.

The circuitry 130 can include components to apply a voltage to the saw blade via the aforementioned third lead, measure the voltage across the conducting layer via the first and second leads, compare the measured voltage across the conducting layer to a threshold value, make a determination that the threshold value is exceeded as a result of the saw blade contacting the conducting layer, and activating the audio alarm 140 and/or visual alarm 140 in response to the determination that the threshold value is exceeded. Any electrical circuit components known in the art may be used to form the circuitry 130. In one embodiment, the circuitry 130, along with the processor 120 and the memory 125, can all be incorporated into a circuit board such as an Arduino. Alternatively, any other type of circuit board and/or individual components may be used. The user interface 145 can include user controls such as an on/off switch, status indicators, and/or a display screen that allows the user to view measured voltages, measured temperature, and/or alerts.

Figure 3:
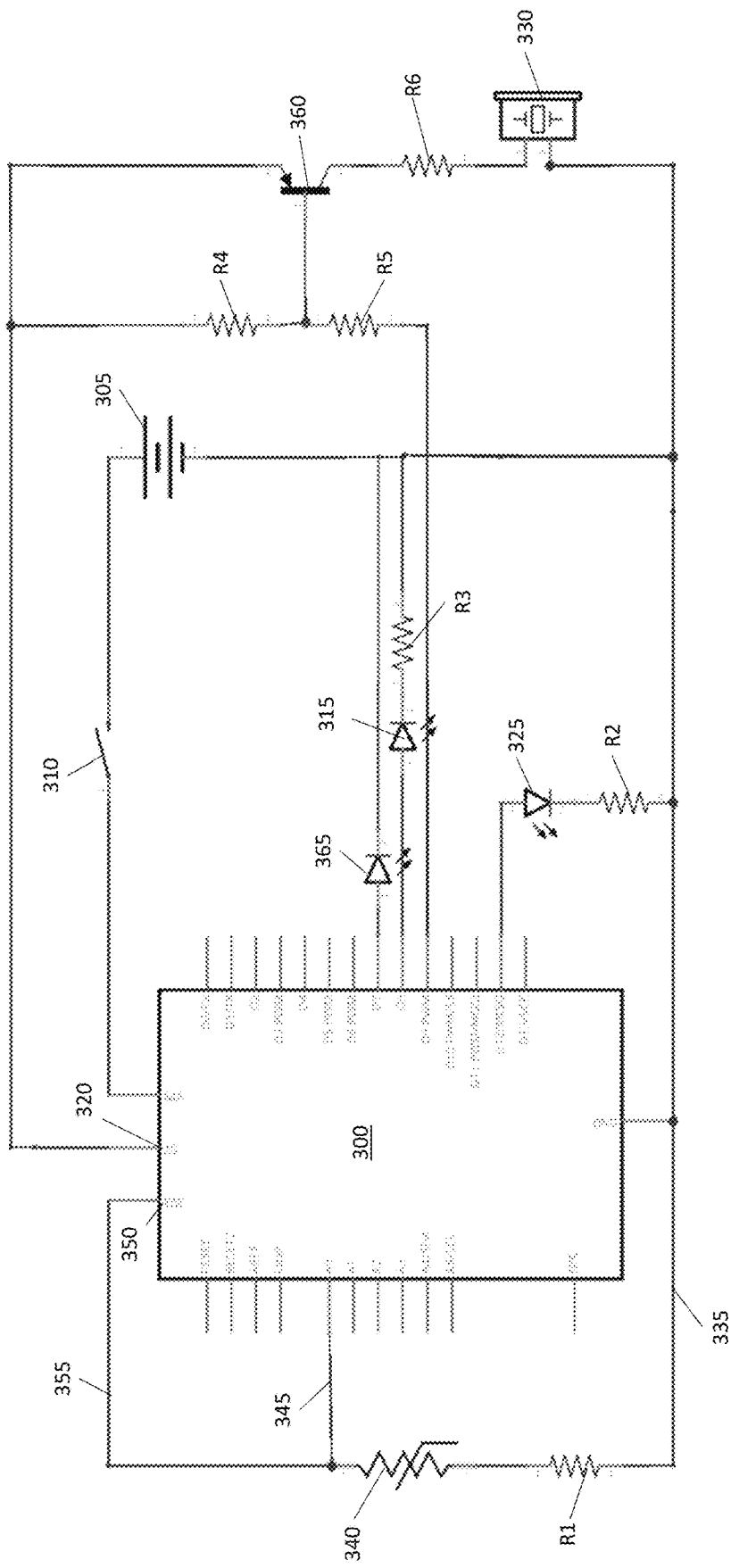
FIG. 3 is a circuit diagram for implementing the cast saw protective system in accordance with an illustrative embodiment.

FIG. 3 is a circuit diagram for implementing the cast saw protective system in accordance with an illustrative embodiment. In alternative embodiments, different circuit components and/or configurations may be used. A microcontroller board 300 includes one or more processors, memory, and other circuit components as discussed below. In one embodiment, the microcontroller board 300 can be an Arduino Uno board. Alternatively, any other board may be used. In another alternative embodiment, individual components may be used in place of a microcontroller board. The microcontroller board 300 receives power at an input port (VIN) by way of a power source 305. The power source 305 can be implemented as a 9V battery. Alternatively, any other power source may be used.

An on/off switch 310 is used to control whether power from the power source 305 is delivered to the microcontroller board 300. When the on/off switch 310 is closed, a power indicator LED 315 is activated to let the operator know i) that the system is on, and ii) that the power source 305 has sufficient charge to the power the system. If the power source 305 is a battery and the battery has lost its charge, the power indicator LED 315 will not light up when the on/off switch 310 is closed, indicating to the operator that the battery is dead and the system will not function. In an illustrative embodiment, the power indicator LED 315 can emit a green light. In an alternative embodiment, the power indicator LED 315 can be a different color or omitted from the system.

A first voltage output 320 from the microcontroller board 300 is used to provide power to the power indicator LED 315, an alarm indicator LED 325, and an audio alarm 330. A first lead 335 extends from a ground port of the microcontroller board 300 to a first end of a conductive layer 340 incorporated into a cast. A second lead 345 extends from a measurement port of the microcontroller board 300 to a second end of the conductive layer 340. A second voltage output 350 is used to provide power to a third lead 355, which is in direct or indirect contact with the saw blade mounted to the cast saw. In one embodiment, the first voltage output 320 can be 5V and the second voltage output 350 can be 3.3V. Alternatively, any other appropriate values may be used.

In operation, a user of the system attaches the first lead 335 and the second lead 345 to opposite ends of the conductive layer 340 of the cast. The user also connects the third lead 355 to the cast saw such that the third lead 355 is in electrical communication with the saw blade. In one embodiment, a nut that holds the saw blade onto the saw can be removed, the third lead 355 can be attached to the carriage of the saw blade, and the nut can be replaced to secure the third lead 355 to the blade. Alternatively, the cast saw can include a receptacle in electrical communication with the saw blade, wherein the receptacle is configured to receive a clip or other component attached to the third lead 355. In another alternative embodiment, the third lead 355 and other components can be incorporated into the cast saw. In such an embodiment, the main power source of the cast saw can be used as the power source 305.

Once connections are made, the user turns the on/off switch 305 into the closed (on) position such that power from the power source 305 is provided to the voltage input of the microcontroller board 300. The microcontroller board 300 determines whether the input received from the power source 305 is adequate to power the system. If the received power is adequate, the microcontroller board 300 turns on the power indicator LED 315 to inform the operator that the system is operational. If the received power is inadequate, the power indicator LED 315 is not activated, which is an indication to the user that the system is not operational. The microcontroller board 300 also utilizes the received power to apply a voltage to the third lead 355 via the second voltage output 350. In one embodiment, the audio alarm 330 and/or alarm indicator LED 325 are activated by the microcontroller board 300 if the microcontroller board determines that the first lead 335 and the second lead 345 are not properly attached to the conductive layer 340. This determination of whether the first and second leads are properly attached can be made based on whether the voltage measured between the first and second leads falls within a predetermined voltage range.

The user then commences to use the cast saw to cut through the cast for removal. During the cutting process, the microcontroller board 300 continuously or intermittently measures the voltage across the conductive layer 340 (relative to ground) using the first lead 335 and the second lead 345. The microcontroller board 300 also monitors this measured voltage to determine if the voltage exceeds a predetermined threshold, such as 200 mV. Alternatively, other threshold values may be used. During normal cutting in which the saw blade does not come into contact with the conductive layer 340, the measured voltage across the conductive layer 340 should remain fairly static and stay under the threshold value. If during the cutting process the saw blade contacts the conductive layer 340, the voltage applied to the saw blade via the third lead 355 will cause an increase in the voltage measured across the conductive layer 340 such that the measured voltage exceeds the threshold. For example, upon contact of the saw blade with the conductive layer 340, the measured voltage can increase to a sum of the inherent voltage across the conductive layer 340 and the voltage resulting from the saw blade contact. The microcontroller board 300 can use a comparator or any other comparison logic/hardware known in the art to determine whether the measured voltage across the conductive layer 340 exceeds the threshold.

In response to a determination that the saw blade has contacted the conductive layer 340, the microcontroller board 300 activates both the alarm indicator LED 325 and the audio alarm 330. In alternative embodiments, only one of the alarm methods may be used. The alarm indicator LED 325 can emit a red light to alert the user that he/she needs to stop the cast saw. Alternatively, a different color may be used. The audio alarm 330 emits a sound that also alerts the user to stop the cast saw. In one embodiment, the audio alarm 330 can be a 120 decibel (dB) continuous sound piezo buzzer alarm speaker. In alternative embodiments, any other type of speaker or noise-emitting device such as a bell, etc. may be used instead. A transistor 360 is incorporated into the system to act as a switch for the audio alarm 330. In alternative embodiments, the transistor 360 may not be used.

As indicated in FIG. 3, the circuitry also includes several resistors to ensure proper operation of the system. In an illustrative embodiment, resistor R1 can have a resistance value of approximately 470 Ohms, resistors R2 and R3 can have a resistance value of approximately 330 Ohms, resistors R4 and R5 can have a resistance value of approximately 1 kiloOhm, and resistor R6 can have a resistance value of approximately 680 Ohms. In alternative embodiments, other resistance values may be used. Also depicted in FIG. 3 is a warning LED 365. In one embodiment in which the power source 305 is a battery, the warning LED 365 can be used to indicate a low battery condition by emitting a yellow light. Alternatively, a different color may be used. In another alternative embodiment, the warning LED 365 may not be used.

The components depicted in FIG. 3 can be included in/on a circuit box or other housing. In one embodiment, with the exception of the leads that connect to the conductive layer, the components depicted in FIG. 3 can be incorporated into the cast saw. For example, the microcontroller 300, the alarm indicator LED 325, the power source 305, the audio alarm 330, etc. can be incorporated into the cast saw itself. In such an embodiment, the cast saw can include receptacles or ports configured to receive the first lead 335 and the second lead 345 such that the voltage across the conductive layer 340 can be measured and monitored. Additionally, the cast saw may be configured to include a plurality of alarm indicator LEDs on a housing of the cast saw. The plurality of alarm indicator LEDs can be positioned such that they will be visible to the saw operator while the saw is in use in any of a number of different orientations.

In an alternative embodiment, the system can also include one or more thermal sensors formed within the cast proximate to the conductive layer. In such an embodiment, one or more leads can be connected from the system controller to the one or more thermal sensors embedded in the cast such that the system controller can monitor the temperature of the cast. If the monitored temperature exceeds a threshold, an audio and/or visual alarm can be activated to inform the operator that the cast saw should be stopped to prevent thermal injury. The temperature threshold can be 120 degrees Fahrenheit, or alternatively another value may be used. One or more thermocouples can also be attached to the saw blade to monitor its temperature, and the user can be alerted if the saw blade exceeds a given threshold temperature. As an example, a thin sheet of copper can be mounted at the edge of the saw blade with a layer of insulating material positioned just above the edge of the saw blade. The thermocouple can be composed of the copper and a relatively constant cold junction point (positioned in an area that is not expected to get hot), and the temperature from the thermocouple can be monitored.

Figure 4:
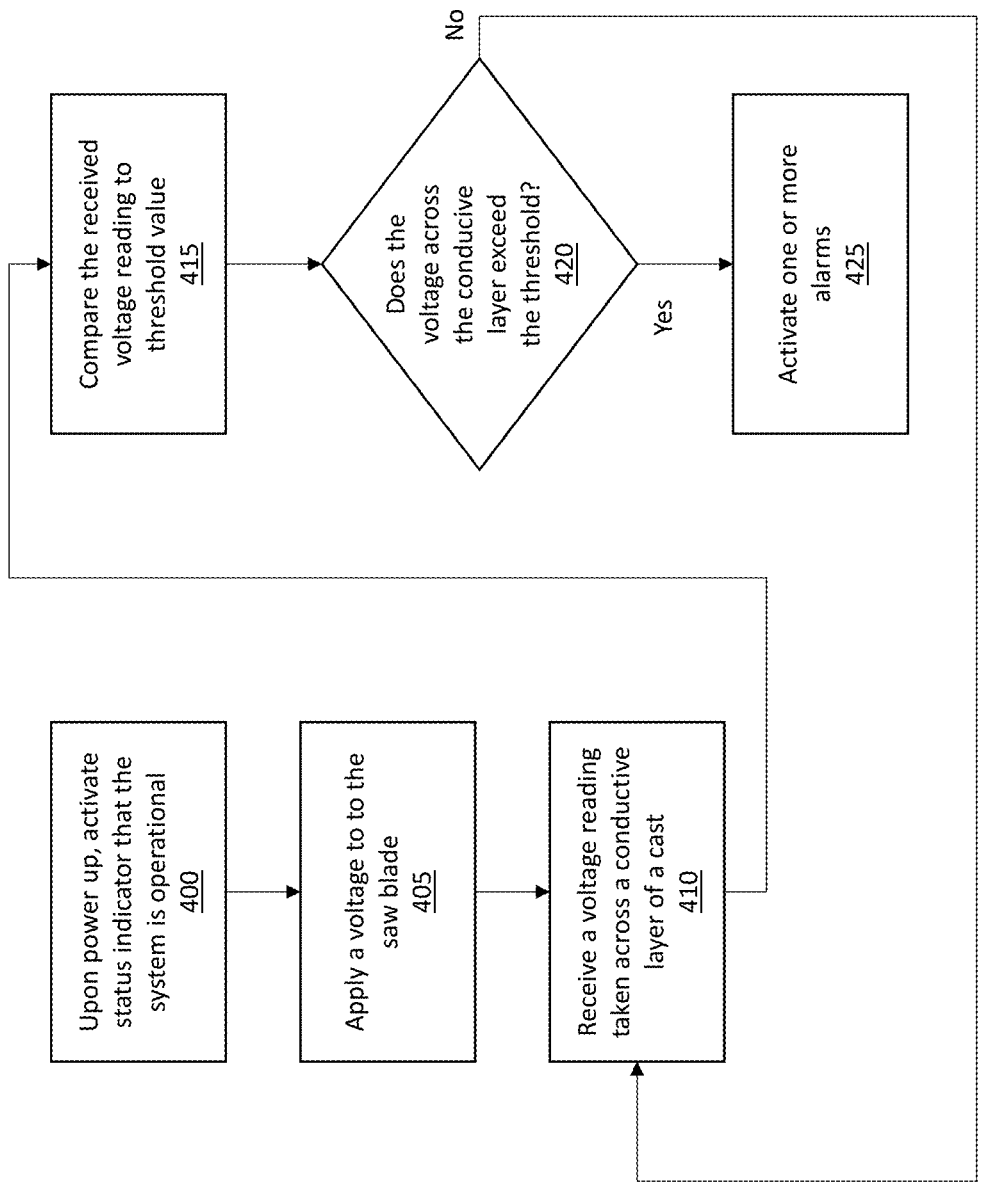
FIG. 4 is a flow diagram depicting operations performed by a cast saw protective system in accordance with an illustrative embodiment.

FIG. 4 is a flow diagram depicting operations performed by a cast saw protective system in accordance with an illustrative embodiment. In alternative embodiments, fewer, additional, and/or different operations may be performed. Additionally, the use of a flow diagram is not meant to be limiting with respect to the order of operations performed. In an operation 400, upon power up of the system, a status indicator is activated to indicate to the user that the system is operational. The status indicator can be the power indicator LED 315 described above, or a different form of indicator may be used. In an alternative embodiment in which the system is incorporated into the cast saw, the status indicator may not be used.

In an operation 405, a voltage is applied to the saw blade. In one embodiment, the voltage can be applied through the third lead 355 by a voltage output of the microcontroller board 300. Alternatively, the system may be incorporated into the cast saw such that an external lead is not used to apply the voltage to the saw blade. In an operation 410, a voltage reading taken across a conductive layer of the cast is received. In an illustrative embodiment, the conductive layer is in the form of a cloth stockinette with a metallic coating. In alternative embodiments, the conductive layer can be a strip of silicon or other conductive material that runs a length of the cast, a conductive wrap, etc. The voltage can be received from first and second leads which are in electrical contact with opposite ends of the conductive layer.

In an operation 415, the received voltage readings are compared to a threshold value, such as 150 mV, 200 mV, 250 mV, etc. The comparison can be performed by any logic and/or hardware known in the art. In an operation 420, a determination is made regarding whether the measured voltage across the conductive layer exceeds the threshold value. If a determination is made that the voltage exceeds the threshold, this indicates that the saw blade has contacted the conductive layer, and one or more alarms is activated in an operation 425. The one or more alarms can be visual and/or audio alarms as described herein. The alarm(s) inform the user that he/she should either stop the saw or ensure that the saw does not cut any deeper. If a determination is made in operation 420 that the voltage does not exceed the threshold, the system again proceeds to implement the operations 410, 415, and 420.

Figure 5:
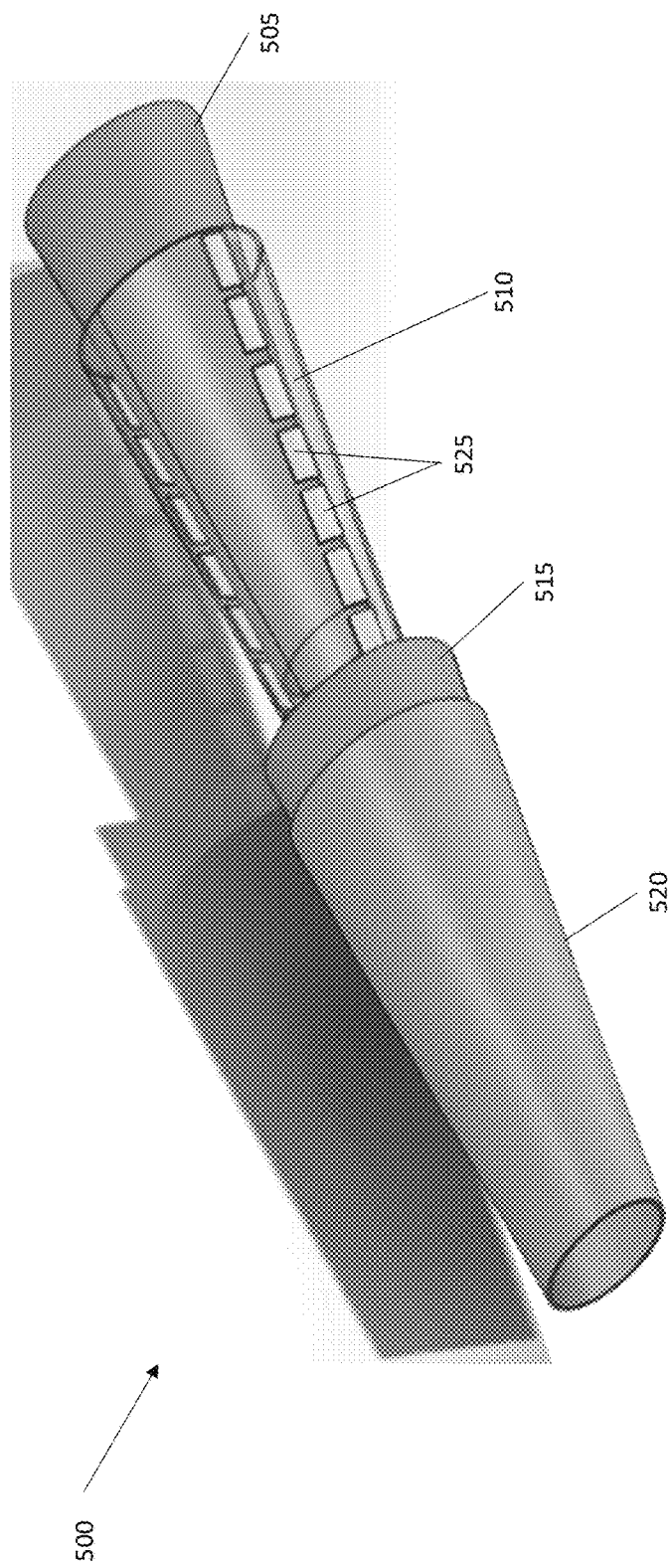
FIG. 5 shows dye packets incorporated into a cast in accordance with an illustrative embodiment.

In an alternative embodiment, dye packets can be incorporated into the cast, and upon contact from the saw blade, the contacted dye packet can rupture and release a dye to inform the user that the saw has penetrated too far. The dye packets can be used alone, or in conjunction with any of the other systems described herein. FIG. 5 shows dye packets incorporated into a cast in accordance with an illustrative embodiment. As shown in FIG. 5, a cast 500 includes a first cotton layer 505, a dye layer 510, a second cotton layer 515, and a hard exterior layer 520. In one embodiment, the first cotton layer 505 can be a net/mesh layer and the second cotton layer 515 can be a padding layer. Alternatively, both of the cotton layers can be padding layers. The dye layer 510 is incorporated between the first cotton layer 505 and the second cotton layer 515.

The dye layer 510 includes a plurality of dye packets 525. Multiple dye packets are used such that multiple indications can be provided to the user as the user moves the saw along the length of the cast. If a single (large) dye packet were used, the user would be informed of an initial deep cut, but not of any subsequent cuts that go to deep. In the embodiment of FIG. 5, the dye packets are arranged in lines running the length of the cast, and the lines of dye packets are positioned along the portion(s) of the cast that will be cut by the cast saw. In an alternative embodiment, the dye packets can be evenly distributed within the entire area of the cast. In another embodiment, the dye layer 510 can be in the form of a sheet, similar to bubble wrap, that includes a plurality of dye packets in place of air bubbles, where the dye packets are connected to one another via a breathable material. In another embodiment, the dye layer 510 can be in the form of one or more strips of dye packets that are inserted into the cast.

In another illustrative embodiment, the dye used in the embodiment of FIG. 5 can be a colored lubricant. As a result, when the saw blade contacts the dye, the saw blade is lubricated and the physical resistance between the saw blade and the cast is reduced. This reduces the temperature of the saw blade and helps to reduce the likelihood of a thermal injury to the patient.

Described herein are a plurality of systems and methods for improving patient safety during a cast removal process. While some embodiments were described with reference to an arm cast, it is to be understood that the disclosed embodiments are not limited to arm casts, but can be used with any type of cast that can be removed with the use of a cast saw. It is also to be understood that any specific hardware components referenced herein are meant to be illustrative, and that in alternative embodiments other comparable components may be used.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method comprising:
    applying, by a processor coupled to a voltage source, a voltage to a saw blade of a cast saw;
    receiving a voltage reading taken across a first lead connected to a first end of a conductive layer and a second lead connected to a second end of the conductive layer, wherein the conductive layer is embedded with a cast that is to be sawed open by the cast saw, and wherein the conductive layer is designed to have an inherent measurable voltage across a surface of the conductive layer;
    determining, by the processor, whether the received voltage reading exceeds a threshold voltage, wherein the threshold voltage is based at least in part on the inherent measurable voltage across the surface of the conductive layer, wherein the inherent measurable voltage helps to determine whether the first and second leads are properly attached to the conductive layer; and responsive to a determination that the received voltage
    exceeds the threshold voltage, activating an alarm to warn a user of the cast saw that the saw blade is in contact with the conductive layer.

2. The method of claim 1, wherein the alarm comprises an audio alarm that emits a sound to warn the user.

3. The method of claim 1, wherein the alarm comprises a visual alarm in the form of a light to warn the user.

4. The method of claim 1, wherein the voltage is applied to the saw blade by way of a lead that is in electrical contact with the saw blade.

5. The method of claim 1, further comprising activating, by the processor, a power indicator configured to indicate whether the voltage source is sufficient to operate the protective system.

6. The method of claim 1, wherein the conductive layer comprises a cloth with a metallic coating.

7. The method of claim 6, wherein the metallic coating comprises silver.

8. A protective system for a cast saw having a saw blade for cutting a cast, said protective system comprising: a voltage source;
    a conductive layer designed to have an inherent measurable voltage across a surface of the conductive layer;
    a first lead attached to a first end of the conductive layer that is at least partially embedded in the cast, and a second lead attached to a second end of the conductive layer; and
    a processor coupled to the voltage source, wherein the processor is configured to:
        apply a voltage to the saw blade of the cast saw;
        receive a voltage reading taken across the conductive layer, wherein the received voltage reading comprises a measurement taken across the first lead and the second lead;
        determine whether the received voltage reading exceeds a threshold voltage, wherein the threshold voltage is based at least in part on the inherent measurable voltage across the surface of the conductive layer, wherein the inherent measurable voltage helps to determine whether the first and second leads are properly attached to the conductive layer; and
        responsive to a determination that the received voltage
        exceeds the threshold voltage, activate an alarm to warn a user of the cast saw that the saw blade is in contact with the conductive layer.

9. The protective system of claim 8, further comprising a third lead that is in electrical contact with the saw blade, wherein the voltage applied to the saw blade is applied through the third lead.

10. The protective system of claim 8, wherein the conductive layer comprises one or more strips of material that include at least silicon.

11. The protective system of claim 8, wherein the threshold voltage comprises 200 milliVolts.

12. The protective system of claim 8, wherein the alarm comprises an audio alarm that emits a sound to warn the user.

13. The protective system of claim 8, wherein the alarm comprises a visual alarm in the form of a light to warn the user.

14. The protective system of claim 8, wherein the conductive layer comprises a cloth with a metallic coating, and wherein the metallic coating comprises silver.

15. The protective system of claim 8, further comprising one or more thermal sensors incorporated into the cast.

16. The protective system of claim 8, wherein the processor and the alarm are incorporated into the cast saw.

17. The protective system of claim 8, further comprising a power indicator configured to indicate whether the voltage source is sufficient to operate the protective system.

18. The protective system of claim 8, further comprising a plurality of dye packets incorporated into the cast.

19. The protective system of claim 8, wherein the inherent measurable voltage is less than 200 milliVolts.

* * * * *